(12) United States Patent
Lee

(10) Patent No.: US 11,511,004 B2
(45) Date of Patent: Nov. 29, 2022

(54) TOILET EQUIPPED WITH INFRARED GENERATOR

(71) Applicant: Jun Gue Lee, Incheon (KR)

(72) Inventor: Jun Gue Lee, Incheon (KR)

(*) Notice: Subject to any disclaimer, the term of this patent is extended or adjusted under 35 U.S.C. 154(b) by 0 days.

(21) Appl. No.: 17/299,525

(22) PCT Filed: Aug. 20, 2019

(86) PCT No.: PCT/KR2019/010602
§ 371 (c)(1),
(2) Date: Jun. 3, 2021

(87) PCT Pub. No.: WO2020/251114
PCT Pub. Date: Dec. 17, 2020

(65) Prior Publication Data
US 2022/0096671 A1    Mar. 31, 2022

(30) Foreign Application Priority Data

Jun. 12, 2019 (KR) .......... 10-2019-0069588
Jun. 17, 2019 (KR) .......... 10-2019-0071301

(51) Int. Cl.
*A61L 2/08*      (2006.01)
*E03D 11/13*     (2006.01)

(52) U.S. Cl.
CPC .......... *A61L 2/085* (2013.01); *E03D 11/13* (2013.01)

(58) Field of Classification Search
CPC .......... E03D 11/02; E03D 11/13; E03D 9/00; A61N 5/06; A61L 2/085
USPC .......... 4/222, 233, 661
See application file for complete search history.

(56) References Cited

U.S. PATENT DOCUMENTS

| | | | | |
|---|---|---|---|---|
| 2,947,850 | A * | 8/1960 | Reilly | E03D 11/06 362/154 |
| 5,513,396 | A * | 5/1996 | Tsipov | E03D 9/00 4/420 |
| 5,915,845 | A * | 6/1999 | Lee | A47K 13/30 4/233 |
| 6,408,459 | B1 * | 6/2002 | Lee | E03D 11/02 4/233 |

(Continued)

FOREIGN PATENT DOCUMENTS

| | | |
|---|---|---|
| CN | 108589869 | 9/2018 |
| JP | 2005-307622 | 11/2005 |

(Continued)

*Primary Examiner* — David P Angwin
*Assistant Examiner* — William R Klotz
(74) *Attorney, Agent, or Firm* — Revolution IP, PLLC

(57) ABSTRACT

The present invention relates to a toilet equipped with an infrared generator. The toilet equipped with an infrared generator is fabricated by separately forming a toilet body provided with an infrared generator in one side surface thereof, a bowl made of a material through which infrared rays emitted by the infrared generator can be transmitted and furnished with an infrared ray transmission region without the formation of a hole, and a rim conduit and then coupling the infrared generator, the bowl, and the rim conduit to the separately formed toilet body. The toilet equipped with an infrared generator enables the infrared generator to be easily installed without forming a hole into the bowl, and can prevent excretions, such as urine and feces, from leaking to the infrared generator.

15 Claims, 17 Drawing Sheets

(56) References Cited

U.S. PATENT DOCUMENTS

| | | | |
|---|---|---|---|
| 6,601,247 B2* | 8/2003 | Shimizu | G02B 6/0014/584 |
| 9,146,032 B2* | 9/2015 | Maxwell | F21V 33/004 |
| 9,371,136 B2* | 6/2016 | Beach | E03F 1/006 |
| 9,861,239 B1* | 1/2018 | Robinson | A47K 13/302 |
| 11,180,910 B2* | 11/2021 | Ahola | E03D 1/26 |
| 2007/0012491 A1 | 6/2007 | Davies et al. | |
| 2009/0107178 A1* | 4/2009 | Chables Sandoval | C03C 1/1065/61 |
| 2009/0216099 A1* | 8/2009 | Kim | A61B 5/25 600/509 |
| 2015/0074887 A1* | 3/2015 | Theuerl | A61L 2/22 4/222 |
| 2018/0007323 A1 | 3/2018 | Hall et al. | |
| 2018/0070926 A1* | 3/2018 | Hall | G01N 21/251 |
| 2018/0153414 A1* | 6/2018 | Hall | A61B 5/0082 |
| 2021/0140160 A1* | 5/2021 | Lee | E03D 11/13 |
| 2021/0379217 A1* | 12/2021 | Beckman | A61L 2/24 |

FOREIGN PATENT DOCUMENTS

| | | |
|---|---|---|
| JP | 2007-255160 | 10/2007 |
| KR | 20-0262727 | 1/2002 |
| KR | 10-2001-0025666 | 7/2002 |
| KR | 20-0425176 | 8/2006 |
| KR | 10-0755084 | 8/2007 |
| KR | 10-1899759 | 9/2018 |
| KR | 10-1899762 | 10/2018 |

* cited by examiner

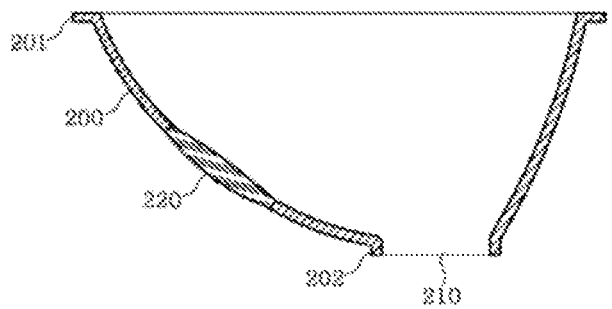
FIG. 7A(1)
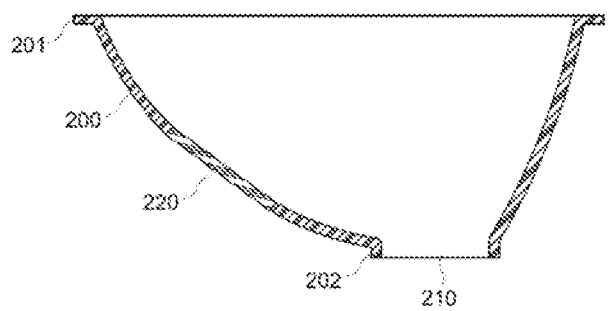
FIG. 7A(2)
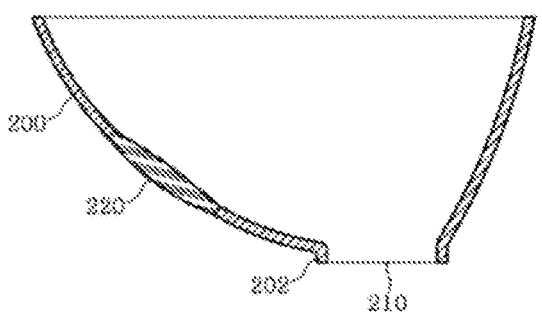
FIG. 7B(1)
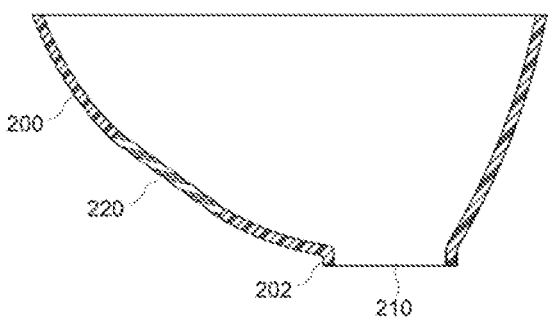
FIG. 7B(2)

TOILET EQUIPPED WITH INFRARED GENERATOR

CROSS-REFERENCE TO RELATED APPLICATIONS

This application is a national stage application of International Patent Application No. PCT/KR2019/010602 filed on Aug. 20, 2019, which claims priority to Korean Patent Application No. 10-2019-0069588 filed on Jun. 12, 2019 and Korean Patent Application No. 10-2019-0071301 filed on Jun. 17, 2019, the entire contents of which are incorporated by reference herein.

TECHNICAL FIELD

The present invention relates generally to a toilet equipped with an infrared generator, and more specifically to a toilet equipped with an infrared generator, which, in order to provide a toilet with an infrared generator without forming a hole into a bowl, is fabricated by separately forming a toilet body provided with an infrared generator in one side surface thereof, a bowl made of a material through which infrared rays emitted by the infrared generator can be transmitted and furnished with an infrared ray transmission region without the formation of a hole, and a rim conduit and then coupling the infrared generator, the bowl, and the rim conduit to the separately formed toilet body.

BACKGROUND

General, toilets equipped with an infrared generator are used to prevent or treat various types of diseases by radiating infrared rays onto the genital and anal region of a user.

Examples of such technology are disclosed in Korean Patent No. 10-0755084 (patent document 1) and Korean Utility Model Registration No. 20-0425176 (patent document 2).

Patent document 1 discloses a toilet in which an infrared ray lamp fastening device is installed in an installation hole formed in one side of a toilet body, the toilet including: a casing at the upper end of the inside of which is formed a stop protrusion; a socket cover which is integrated with the lower end of the casing, and inside which is formed a socket in which an infrared lamp can be mounted; a heat-proof lens cover which has a coupling member configured to be fastened to the stop protrusion at the upper end of the inside of the casing and which is equipped with a heat-proof lens configured to radiate infrared rays of the infrared lamp into the toilet body; and a water leakage prevention packing which is disposed between the heat-proof lens and the casing and which keeps the inside of the toilet body watertight.

Patent document 2 discloses a far-infrared lamp fastening structure for a far-infrared toilet, the far-infrared lamp fastening structure including: a toilet 100; a "U"-shaped far-infrared lamp insertion portion 110 which protrudes to the lower portion of the front of the toilet 100 and into which a far-infrared lamp is inserted; a far-infrared lamp fastening device which is contained inside the far-infrared lamp insertion portion 110; a sensor 80 which is contained and installed on one side surface of the lower portion of the front of the toilet 100; and the far-infrared lamp 6 which is inserted into the far-infrared lamp insertion portion 110, and which is fastened by the far-infrared lamp fastening device.

However, the above-described conventional technology is formed in a structure in which a hole is formed in the inner wall of the toilet body, the far-infrared lamp is installed in the hole, and far-infrared rays are radiated into the toilet body. Accordingly, the conventional technology is problematic in that it is difficult and complicated to form the hole, and thus a long manufacturing time is required, thereby increasing manufacturing cost.

Furthermore, although the packing is disposed between the hole and the far-infrared lamp, the packing is easily damaged due to the repetitive expansion and contraction of the packing attributable to the season, and thus urine and feces leak through a gap around the packing, thereby causing the problem in which the infrared lamp is damaged.

SUMMARY

The present invention has been conceived to overcome the above-described problems, and an object of the present invention is to provide a toilet equipped with an infrared generator, which is fabricated by separately forming a toilet body provided with an infrared generator in one side surface thereof, a bowl made of a material through which infrared rays emitted by the infrared generator can be transmitted and furnished with an infrared ray transmission region without the formation of a hole, and a rim conduit, coupling the bowl inside the toilet body, and coupling the rim conduit to the top of the toilet body inside which the bowl has been coupled, thereby enabling the infrared generator to be easily installed in the toilet without forming a hole into the bowl and also preventing excretions, such as urine and feces, from leaking to the infrared generator.

Another object of the present invention is to provide a toilet equipped with an infrared generator, in which the inner or outer surface of a bowl is coated with an infrared generation material, or upon the formation of a bowl, an infrared generation material is added to the material of the bowl and then the bowl is formed, thereby enabling the quantity of infrared rays to be emitted to the inner surface of the bowl to increase and also enabling infrared rays to be continuously emitted.

In order to accomplish the above objects, the present invention provides a toilet equipped with an infrared generator, the toilet including: a toilet body (100) the top of which is open, and in one side surface of which is formed an opening (120) configured to provide an infrared generator therein; a bowl (200) which is coupled inside the toilet body (100), which is made of a material capable of transmitting infrared rays, emitted by the infrared generator (400), therethrough, and in which an infrared ray transmission region (220), through which infrared rays emitted by the infrared generator (400) are transmitted, is formed without the formation of a hole; and a rim conduit (300) which is coupled to the top of the toilet body (100) inside which the bowl (200) has been coupled; wherein the toilet body (100), the bowl (200), and the rim conduit (300) are separately formed, and are then integrated into a single body; and wherein the infrared generator (400) is provided in the opening (120) of the toilet body.

A first bent protrusion (201) configured to be coupled to the top surface of the toilet body (100) may be formed along the circumference of the upper end of the bowl (200), and a second bent protrusion (202) configured to be coupled to a stepped portion (111) formed on the inner surface of the upper end of a trap (110) may be formed along the circumference of the lower end of the bowl (200).

A stepped part protruding downward may be formed on the outer side of the bottom of the rim conduit (300) which is coupled to the tops of the toilet body (100) and the bowl (200); a first seating protrusion (301) may protrude downward from the outer side of the bottom of the rim conduit (300) by means of the stepped part; and the outer surface of the first seating protrusion (301) may form the same outer surface as the outer surface of the toilet body (100).

A second seating protrusion (330) protruding downward may be formed on the inner side of the bottom of the rim conduit (300) which is coupled to the tops of the toilet body (100) and the bowl (200); the outer surface of the second seating protrusion (330) may be attached to the inner surface of the top of the bowl (200); and the rim conduit (300) may be coupled to the toilet body (100) and the bowl (200) in a state of surrounding the toilet body (100) and the bowl (200) by the second seating protrusion (330).

A support (150) configured to support the bowl (200) may be provided on the bottom of the inside of the toilet body (100); and a connection element (160) configured to connect the bowl (200) and the trap (110) may be provided on the top of the support (150).

A finishing member (700) may be attached to the circumference of the adhered surfaces of the toilet body (100) and the rim conduit (300).

The bowl (200) may be formed in any one of transparent, translucent, and opaque colors through which infrared rays emitted by the infrared generator (400) are transmitted.

The translucent or opaque color in which the bowl (200) is formed may be formed by coating the inner or outer surface of the bowl (200) with an infrared generation material.

The translucent or opaque color in which the bowl (200) is formed may be formed by an infrared generation material added during the injection molding of the bowl (200).

The bowl (200) may be made of any one of glass, plastic, and ceramic.

The infrared ray transmission region (220) and the area of the bowl (200) other than the infrared ray transmission region (220) may be formed in an integrated manner during a bowl formation process, the infrared ray transmission region (220) may be made of a heat-resistant material capable of withstanding high-temperature infrared rays emitted by the infrared generator (400), and the area other than the infrared ray transmission region (220) may be made of a plastic or ceramic material.

The part of an inner surface of the bowl (200) where the infrared ray transmission region (220) is formed may be formed in a planar shape, and the area other than the infrared ray transmission region (220) may be formed in a concave arc shape.

The part of an inner surface of the bowl (200) where the infrared ray transmission region (220) is formed may be formed in a convex shape like a convex lens, and the area other than the infrared ray transmission region (220) may be formed in a concave arc shape.

The infrared generator (400) may be provided inside an outer cover (500); and the outer cover (500) inside which the infrared generator (400) has been provided may be provided in the opening (120).

A coupling means may be provided on the outer circumferential surface of the outer cover (500) to be coupled and fastened into the opening (120); and a fastening means corresponding to the coupling means provided on the outer circumferential surface of the outer cover (500) may be provided on an inner surface of the opening (120).

The opening (120) may be further provided with a fastening element (600); and the infrared generator (400) or the outer cover (500) inside which the infrared generator (400) has been provided may be inserted and fastened into the fastening element (600).

A coupling means may be provided on the outer circumferential surface of the outer cover (500) to be coupled and fastened into the fastening element (600); and a fastening means corresponding to the coupling means formed on the outer circumferential surface of the outer cover (500) may be provided on the inner surface of the fastening element (600).

The coupling means may include any one of a rubber packing configured to be inserted and coupled into the outer circumferential surface of the outer cover (500) and a plurality of protrusions configured to protrude from the outer circumferential surface of the outer cover (500).

The coupling means may include a fastening screw; and the fastening means may include a fastening screw corresponding to the fastening screw of the coupling means.

The coupling means may include fastening slits; and the fastening means may include fastening protrusions corresponding to the fastening slits of the coupling means.

The coupling means may include a magnet member; and the fastening means may include a metallic member (124) corresponding to the magnet member of the coupling means.

The coupling means may include: a plurality of reception depressions which is formed to a predetermined depth; a cylindrical case which is detachably coupled into each of the reception depressions; a pressing protrusion which is movably disposed inside the case; and a spring which performs an elastic action in response to an impact applied to the pressing protrusion.

The fastening element (600) may include: a support portion (620) which supports an area around the infrared ray transmission region (220) of the bowl (200); and a stepped portion (611) which is coupled to an area around the opening (120).

The fastening element (600) may include: a body portion (610) which is provided with a stop portion (612) having a stepped portion (611) which is coupled to an area around the opening (120); and a support portion (620) which protrudes and extends outward from an end of the body portion (610), and which comes into surface contact with a bottom surface of the bowl (200).

An outer circumferential portion (520) having a coupling groove (521) into which an outer end of the fastening element (600) is inserted and coupled may be formed the outer surface of the outer cover (500).

The toilet equipped with an infrared generator according to the present invention is fabricated by coupling the bowl made of a material through which infrared rays emitted by the infrared generator can be transmitted to the toilet body and then coupling the rim conduit to the top of the bowl, thereby providing the effects of enabling the infrared generator to be easily installed without forming a hole into the bowl and preventing excretions, such as urine and feces, from leaking to the infrared generator.

Furthermore, the inner or outer surface of the bowl is coated with the infrared generation material, or upon the formation of the bowl, the infrared generation material is added to the material of the bowl and then the bowl is formed, so that the quantity of infrared rays beneficial to the human body can be increased and also infrared rays can be continuously emitted, thereby improving disease treatment and prevention effects.

BRIEF DESCRIPTION OF THE DRAWINGS

FIGS. 7A(1), 7A(2), 7B(1), and 7B(2) are sectional views showing a bowl according to the present invention

DETAILED DESCRIPTION OF THE DISCLOSURE

Embodiments of the present invention will be described in detail below with reference to the accompanying drawings.

The most preferred embodiments of the present invention will be described in detail below in order to describe the present invention in detail so that those having ordinary skill in the art to which the present invention pertains can easily practice the present invention.

Figure 1:
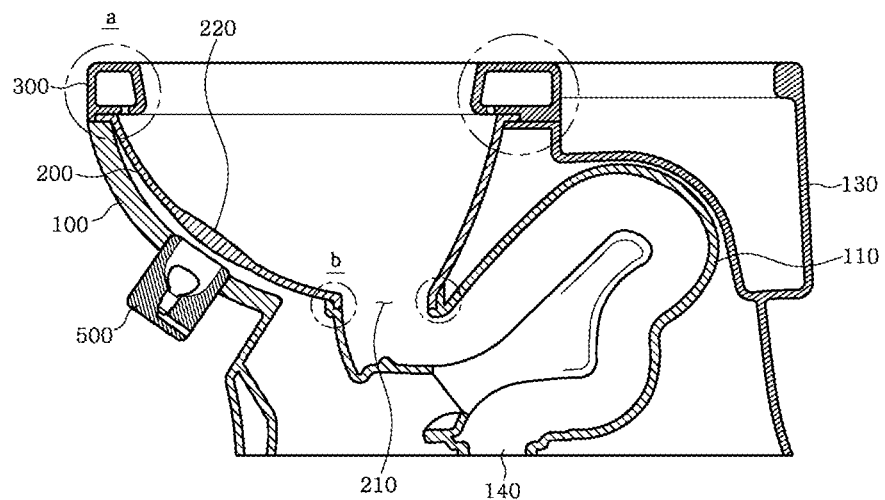
FIG. 1 is a sectional view showing a toilet equipped with an infrared generator according to the present invention.
Figure 2:
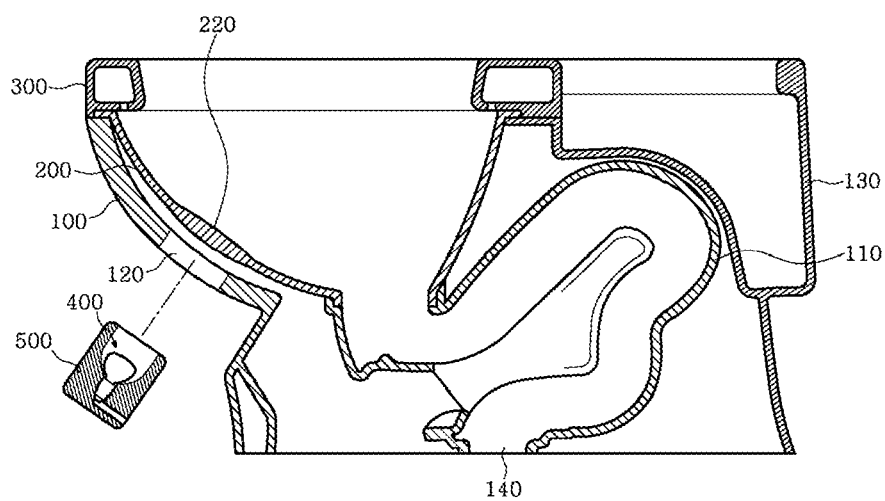
FIG. 2 is a sectional view showing a state in which an outer cover, in which an infrared generator according to the present invention is provided, has been separated.

As shown in FIGS. 1 and 2, a toilet equipped with an infrared generator according to the present invention includes: a toilet body 100 which is provided with an infrared generator 400 in one side surface thereof; a bowl 200 which is coupled inside the toilet body 100; and a rim conduit 300 which is coupled to the top of the toilet body 100 inside which the bowl 200 has been coupled.

In particular, the toilet equipped with an infrared generator according to the present invention is fabricated in such a manner that the toilet body 100, the bowl 200, and the rim conduit 300 are separately formed and then integrated with one another.

A common toilet except for a toilet cover is made of pottery, and a trap, a bowl, and a rim conduit are integrated with the toilet body. Due to this structure, a hole is formed through a toilet body and a bowl in order to install an infrared generator in a toilet. However, it is difficult and complicated to form the hole, and excretions, such as urine and feces, may leak through the gap between the hole and the infrared generator.

In order to prevent these problems, according to the present invention, the bowl 200 made of a material through which infrared rays emitted by the infrared generator 400 are transmitted and furnished with an infrared ray transmission region 220, through which infrared rays emitted by the infrared generator 400 are transmitted, without the formation of a hole is coupled inside the toilet body 100 in one side surface of which is formed an opening 120 in which the infrared generator is provided, the rim conduit 300 is coupled to the circumference of the top of the toilet body 100 inside which the bowl 200 has been coupled, and the infrared generator 400 is inserted and coupled into the opening 120 formed in the toilet body 100.

According to the present invention, the above-described coupling structure of the toilet enables the infrared generator 400 to be easily installed without forming a hole into the bowl 200, and prevents excretions, such as urine and feces, from leaking to the infrared generator 400.

A trap 110 which is interconnected to the drain hole 210 of the bowl 200 is formed inside the toilet body 100.

Furthermore, the toilet body 100 is provided with a water tank 130 in which water is accommodated, and excretions discharged from the bowl 200 are discharged to a drain outlet 140 through the trap 110.

Figure 3A:
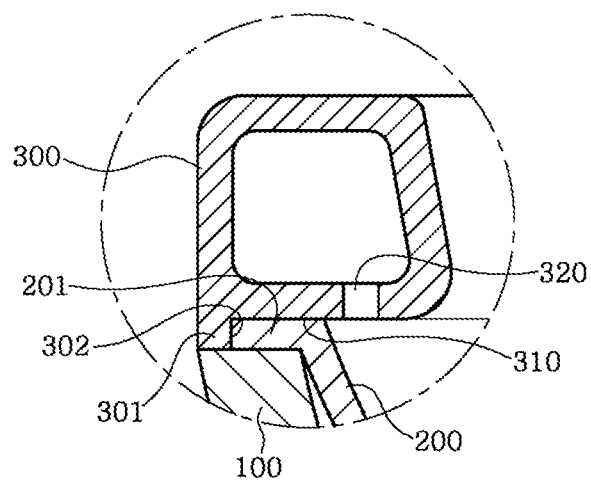
FIGS. 3A and 3B show enlarged views of portions 'a' of FIG. 1.
Figure 3B:
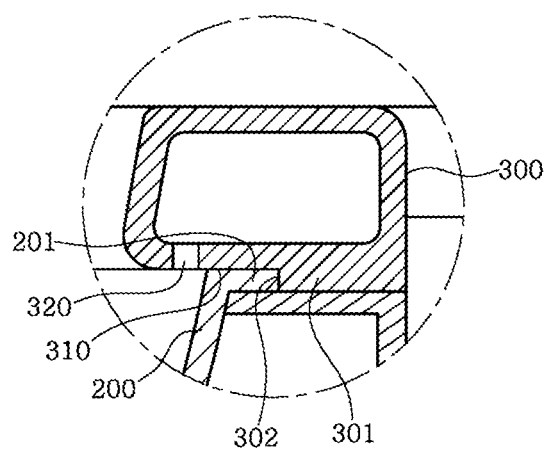
Figure 4A:
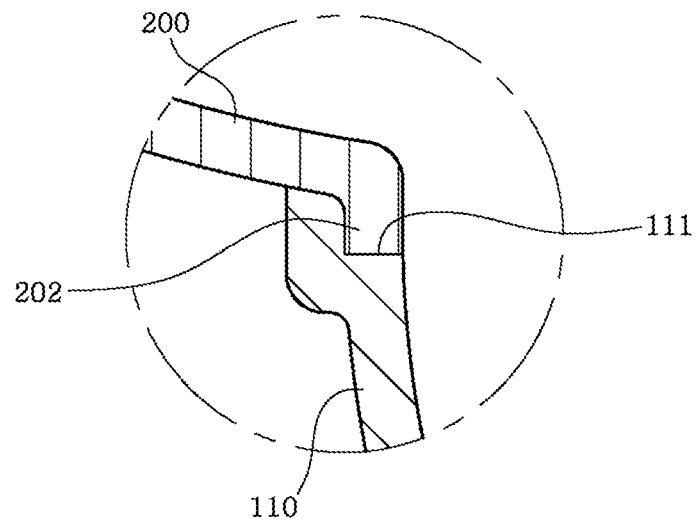
FIGS. 4A and 4B show enlarged views of portions 'b' of FIG. 1.
Figure 4B:
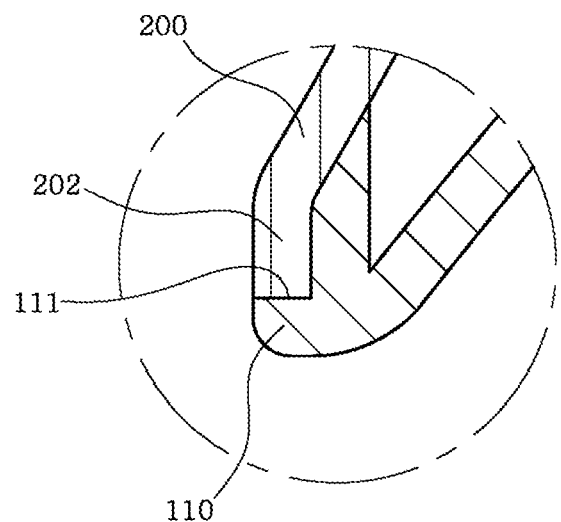

As shown in FIGS. 3 and 4, a first bent protrusion 201 extending and bent in a horizontal direction is formed along the circumference of the upper end of the bowl 200, and a second bent protrusion 202 extending and bent in a vertical direction is formed along the circumference of the lower end of the bowl 200.

The first bent protrusion 201 is coupled to the top surface of the toilet body 100, and the second bent protrusion 202 is coupled to a stepped portion 111 formed on the inner surface of the upper end of the trap 110, which will be described later.

In this case, the second bent protrusion 202 forms the same vertical surface as the inner surface of the upper portion of the trap 110. For this purpose, the thickness of the second bent protrusion 202 is formed to be the same as the area of the stepped portion 111.

The stepped portion 111, to which the second bent protrusion 202 of the bowl 200 is coupled, is formed on the inner surface of the upper end of the trap 110 formed inside the toilet body 100.

The lower end of the bowl 200 is accurately coupled to the upper end of the trap 110 by forming the stepped portion 111 as described above, and this coupling allows the bowl 200 to come into closer contact with the trap 110 and makes the smoothness between the bowl 200 and the trap 110 uniform.

An adhesive may be applied between the top surface of the toilet body 100 and the first bent protrusion 201 and between the stepped portion 111 and the second bent protrusion 202.

The first bent protrusion 201 may be securely fastened to the top surface of the toilet body 100, and the second bent protrusion 202 may be securely fastened to the stepped portion 111 by the adhesive force of the adhesive. It is preferable that an epoxy adhesive be used as the adhesive. The epoxy adhesive may be replaced with a component which provides adhesive force equivalent to that of the epoxy adhesive.

The outer side of the bottom of the rim conduit 300 protrudes downward, and forms a difference in height. This difference in height allows a first seating protrusion 301 to protrude downward from the outer side of the bottom of the rim conduit 300.

In this case, the outer surface of the first seating protrusion 301 of the rim conduit 300 preferably forms the same outer surface as the outer surface of the toilet body 100.

The first seating protrusion 301 of the rim conduit 300 is configured such that the bottom surface thereof is seated on the top surface of the toilet body 100, and a vertical surface 302 formed on the inside of the first seating protrusion 301 of the rim conduit 300 is coupled to the outer surface of the first bent protrusion 201 of the bowl 200.

Furthermore, a seating surface 310 which is seated on the top surface of the first bent protrusion 201 of the bowl 200 is formed on the bottom surface of the rim conduit 300 except for the first seating protrusion 301, and a discharge hole 320 which communicates with the rim conduit 300 is formed through the seating surface.

In other words, the first seating protrusion 301 of the rim conduit 300 is seated on the top surface of the toilet body 100, the seating surface 310 of the rim conduit 300 is seated on the top surface of the bowl 200, and the first bent protrusion 201 of the bowl 200 is coupled to the first seating protrusion 301 and seating surface 310 of the rim conduit 300 in a state of being surrounded by the first seating protrusion 301 and seating surface 310 of the rim conduit 300. This coupling can increase the strength of the coupled portions, and can prevent deformation which occurs locally.

In particular, the discharge hole 320 formed in the rim conduit 300 is formed at a location spaced apart inward from the seating surface 310. The reason for this is to allow washing water, which is discharged through the discharge hole 320, to flow along the inner surface of the bowl 200.

Meanwhile, a sealing member may be provided between the vertical surface 302 of the rim conduit 300 and the top surface of the first bent protrusion 201 of the bowl 200. When the rim conduit 300 is coupled to the outer surface of the first bent protrusion 201 through the sealing member, a close contact property is improved.

This improvement of the close contact property provides the effect of preventing water from infiltrating between the rim conduit 300 and the bowl 200.

Furthermore, a sealing member may be provided between the stepped portion 111 of the toilet body 100 and the second bent protrusion 202 of the bowl 200.

The sealing member may be made of hydrophilic rubber. Hydrophilic rubber generally has the characteristic in which ion migration occurs when it comes into contact with water and thus penetration pressure and density decrease, and also has the characteristic in which the volume thereof expands due to the exclusion of ions when it absorbs water and it recovers to its original state after drying The volume of the hydrophilic rubber expands after the hydrophilic rubber has absorbed water. Accordingly, when the hydrophilic rubber is used in a gap or the like, the gap is sufficiently filled with the hydrophilic rubber, and thus the hydrophilic rubber prevents water from infiltrating through the gap, thereby providing an excellent water leakage prevention effect.

Rubber fabricated by using natural rubber and/or synthetic rubber such as butadiene rubber (BR) or styrene butadiene rubber (SBR), a vulcanizing agent, white carbon, and barium sulfate may be used as the hydrophilic rubber.

Figure 5:
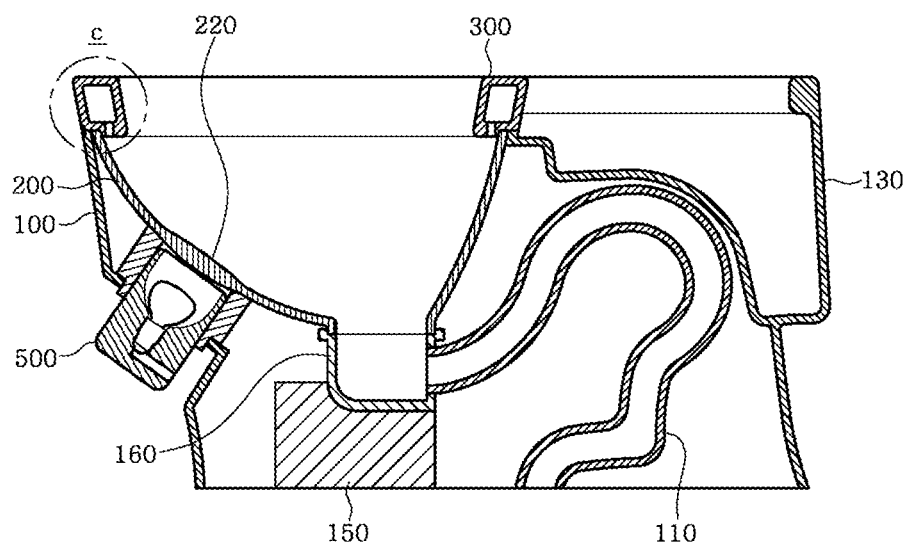
FIG. 5 is a sectional view showing another embodiment of a toilet equipped with an infrared generator according to the present invention.
Figure 6:
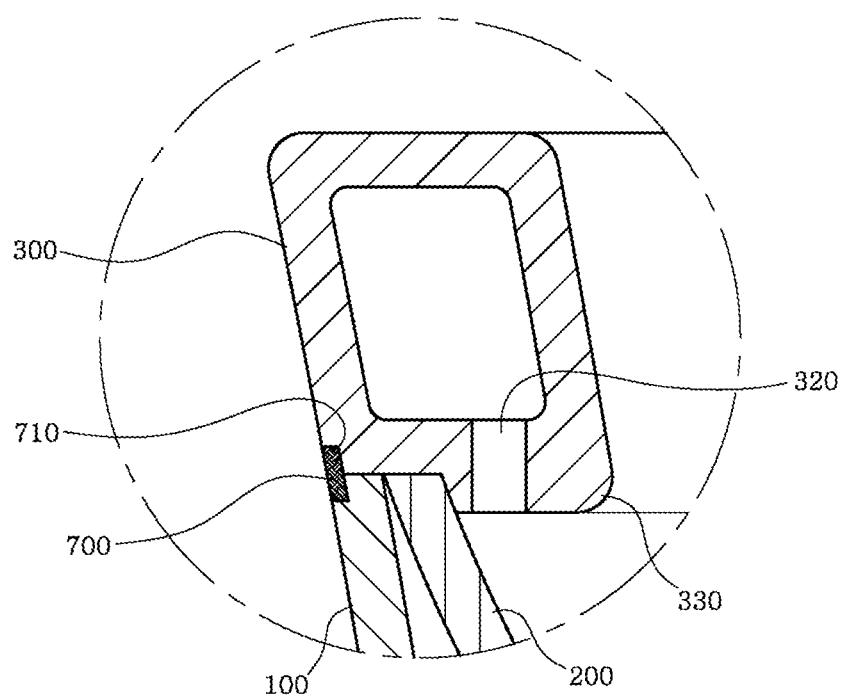
FIG. 6 is an enlarged view of portion 'c' of FIG. 5.

FIGS. 5 and 6 show another embodiment of a toilet equipped with an infrared generator according to the present invention. The toilet equipped with an infrared generator has a structure in which a bowl 200 is coupled inside the toilet body 100 and a second seating protrusion 330 protruding downward is formed on the inside of the bottom of the rim conduit 300 which is coupled to the tops of the toilet body 100 and the bowl 200.

In this case, the formation of the above-described first bent protrusion 201 which extends and is bent from the circumference of the upper end of the bowl 200 in the horizontal direction may be omitted.

The outer surface of the second seating protrusion 330 of the rim conduit 300 is adhered to the inner surface of the upper portion of the bowl 200, and the toilet body 100 and the bowl 200 are coupled to the rim conduit 300 in the form of being surrounded with the rim conduit 300 by the second seating protrusion 330. This coupling can increase the strength of the coupled portions, and can prevent deformation which occurs locally.

Furthermore, a discharge hole 320 may be formed through the second seating protrusion 330 of the rim conduit 300. Washing water discharged through the discharge hole 320 may be allowed to flow along the inner surface of the bowl 200.

However, although the discharge hole 320 may be formed through the second seating protrusion 330 of the rim conduit 300, the present embodiment is not limited thereto. Alternatively, the second seating protrusion 330 of the rim conduit 300 may be formed to protrude from a location spaced apart outward from the inner end of the bottom of the rim conduit 300, and a discharge hole 320 may be formed in the lower portion of the rim conduit 300 inside the second seating protrusion 330 of the rim conduit 300. Accordingly, washing water discharged through the discharge hole 320 may be allowed to flow along the inside of the second seating protrusion 330 and to then flow along the inner surface of the bowl 200.

This provides the effect of preventing water from infiltrating between the rim conduit 300 and the bowl 200 and then infiltrating between the toilet body 100 and the bowl 200.

Meanwhile, a support 150 configured to support the bowl 200 may be provided on the bottom of the inside of the toilet body 100. Furthermore, a connection element 160 configured to connect the bowl 200 and the trap 110 to each other may be provided over the support 150.

The support 150 is a component which is provided on the bottom of the inside of the toilet body 100. The support 150 functions to space and support the connection element 160 apart from the bottom of the toilet body 100.

The connection element 160 is a component which is placed over the support 150. The top of the connection element 160 communicates with the drain hole 210 of the bowl 200, and one side surface of the connection element 160 communicates with the trap 110.

The support 150 and the connection element 160 may be integrated with the toilet body 100 when the toilet body 100 is formed, or may be formed separate from the toilet body 100 and then coupled to the toilet body 100.

A groove 710 may be formed along the outer circumference of the adhered surfaces of the toilet body 100 and the rim conduit 300 according to the present invention in order to allow a finishing member 700 to be attached thereinto.

This provides the effect of making the appearance of the toilet beautiful by finishing the outside of the adhered surfaces of the toilet body 100 and the rim conduit 300 with the finishing member 700.

Although the finishing member 700 may be formed of any one of gold foil, silver foil, and a decorative strip, the present embodiment is not limited thereto. The finishing member 700 may be formed as a plated layer by applying the finishing member 700 into the groove 710.

The bowl 200 according to the present invention may be made of a material through which infrared rays, particularly the light and heat of infrared rays, emitted by the infrared generator 400 can be transmitted. The bowl 200 may be made of one or more selected from various materials such as glass, plastic, ceramic, etc., via which a user can become aware that the light and heat of infrared rays emitted by the infrared generator 400 are transmitted through the bowl 200 by using his or her naked eye and skin.

Furthermore, only the infrared ray transmission region 220 of the bowl 200 may be made of a material capable of transmitting the light and heat of infrared rays emitted by the infrared generator 400, and an overall area except for the infrared ray transmission region 220 may be made of another material.

Meanwhile, the bowl 200 may be formed in any one of transparent, translucent and opaque colors through which infrared rays emitted by the infrared generator 400 can be transmitted.

In this case, the transmission of infrared rays emitted by the infrared generator 400 means that the light and heat of infrared rays emitted by the infrared generator 400 are transmitted. It is sufficient if a user can become aware of it by using his or her naked eye and skin.

Furthermore, although it is sufficient if the translucent or opaque color of the bowl 200 is a color through which the light and heat of infrared rays generated by the infrared generator are transmitted to the internal space of the bowl 200, it is preferable in the present invention to apply a color through which the light and heat of infrared rays generated by the infrared generator are transmitted more desirably. The translucent or opaque color of the bowl 200 may be formed by coating the inside and outside of the formed bowl 200 with a color through which infrared rays are transmitted or by mixing glass, plastic, ceramic, or the like, which is the material of the bowl 200, with a color through which infrared rays are transmitted and then forming the bowl 200. However, a method of forming the translucent or opaque color of the bowl 200 is not necessarily limited to these methods, but the translucent or opaque color of the bowl 200 may be formed by applying various methods.

More specifically, the translucent or opaque color of the bowl 200 may be formed by coating the inner or outer surface of the fabricated bowl 200 with an infrared generation material.

In other words, the powder of the infrared generation material may be fixed on the inner or outer surface of the bowl 200 by applying a coating paint in a state of uniformly distributing the powder of the infrared generation material throughout the inner or outer surface of the bowl 200, or the powder of the infrared generation material may be added to and mixed with a coating paint and then the mixture thereof may be applied to the inner or outer surface of the bowl. In this case, various methods, such as dip coating, spray coating, and roll coating, may be applied as a method of applying an infrared generation material.

As another embodiment, the translucent or opaque color of the bowl 200 may be formed by an infrared generation material which is added during the injection molding of the bowl 200.

In other words, in a process of molding the bowl 200 by using a fabricated mold, the bowl 200 may be molded by adding an infrared generation material emitting infrared rays beneficial to the human body in addition to any one of glass, plastic, and ceramic.

Although the infrared generation material may be made of a mixture of one or more raw materials selected from the group consisting of tourmaline, illite, quartz, silica sand, diamond, volcanic stone, hematite, calcite, sericite, biotite, loess, elvan, jade and charcoal, the present embodiment is not limited thereto. The infrared generation material may be any material as long as it emits infrared rays.

As described above, the present invention continuously emits a large quantity of infrared rays via the infrared generation material applied or added to the bowl 200 as well as the infrared generator 400, thereby providing the effects of preventing bacteria from growing around the toilet and considerably increasing the amount of infrared radiation beneficial to the human body.

Additionally, the overall area of the toilet body 100 other than the bowl 200 may be formed in a translucent or opaque color, and may be made of any one of glass, plastic, and ceramic in the same manner as the bowl 200 or may be made of one of various materials, such as glass, plastic, ceramic, pottery, etc., different from that of the bowl 200.

In this case, the translucent or opaque color in which the toilet body 100 is formed refers to a color through which excretions temporarily accommodated inside the bowl 200 are not visible from the outside of the toilet. The translucent or opaque color may be a color which allows the transmission of infrared rays or a color which prohibits the transmission of infrared rays.

The translucent or opaque color in which the toilet body 100 is formed may include various colors. The appearance of the toilet may be formed in various colors due to the former various colors. Various esthetic effects can be achieved due to the appearance of the toilet formed in various colors. Furthermore, there can be achieved the effect in which excretions temporarily accommodated inside the bowl 200 are not visible from the outside of the toilet.

Meanwhile, the infrared ray transmission region 220 is formed on one side of the bowl 200 without forming a hole in the bowl 200.

The infrared ray transmission region 220 is formed without forming a hole in the bowl 200. The reason for this is to overcome an insanitation problem which is caused by forming a hole in the bowl 200 in order to provide the infrared generator 400 and in which excretions accommodated inside the bowl 200 leak through the gap of the hole formed in the bowl 200 and the toilet is contaminated with the excretions and the problems of the failure and erroneous operation of the infrared generator 400 which occur due to the leakage of excretions.

In other words, by providing the toilet with the infrared generator without forming a hole in the bowl 200, there is provided the effect of preventing an insanitation problem in which excretions accommodated inside the bowl 200 leak and contaminate the toilet and the problems of the failure and erroneous operation of the infrared generator 400 which occur due to the leakage of excretions.

As shown in FIG. 7, according to the present invention, when the bowl 200 is formed, the infrared ray transmission region 220 and the area other than the infrared ray transmission region are formed in an integrated manner without forming the infrared ray transmission region 220, through which infrared rays emitted by the infrared generator 400 can be transmitted, in the form of a hole. In this case, the infrared ray transmission region 220 may be made of a heat-resistant material capable of withstanding high-temperature heat emitted by the infrared generator, and the area other than the infrared ray transmission region 220 may be formed of a plastic or ceramic material.

It is most preferable that the bowl 200 of the toilet equipped with an infrared generator be fabricated such that the bowl 200 is not deformed by high-temperature infrared rays emitted by the infrared generator 400, the bowl 200 can withstand high-temperature infrared rays, and infrared transmittance is not reduced during the transmission of infrared rays.

When the bowl 200 is made of a plastic material, advantages arise in that it is easy to manufacture the bowl 200, the incidence of defective products is low during the manufacture thereof, and it is easy to transport the bowl 200 because there is little concern about the breakage thereof during transportation. However, disadvantages arise in that there is possibility that the bowl 200 may be deformed by high-temperature infrared rays emitted by the infrared generator 400 and the quantity of infrared rays discharged into the internal space of the bowl 200 is reduced because part of infrared rays emitted by the infrared generator 400 is absorbed while passing through the infrared ray transmission region 220 of the bowl 200 and thus infrared transmittance becomes low.

In contrast, when the bowl 200 is made of heat-resistant glass, tempered glass, or the like which can withstand high-temperature infrared rays emitted by the infrared generator 400, is not deformed and does not reduce infrared transmittance, disadvantages arise in that high-level technical skills are required to manufacture the bowl 200, the incidence of defective products is high because the bowl 200 is not uniformly manufactured, and attention needs to be paid to the transportation of the bowl 200.

In order to overcome these problems, the infrared ray transmission region 220 of the bowl 200 may be made of a heat-resistant material, such as heat-resistant glass, tempered glass, or the like, capable of withstanding high-temperature infrared rays emitted by the infrared generator 400, and the area other than the infrared ray transmission region 220 may be made of a plastic or ceramic material. By forming the infrared ray transmission region 200 and the area other than the infrared ray transmission region 220 in an integrated manner during the formation of the bowl 200, the bowl 200 which is not deformed by high-temperature infrared rays emitted by the infrared generator 400 can be manufactured, and the bowl 200 which does not significantly reduce the transmission of infrared rays when infrared rays emitted by the infrared generator 400 pass through the infrared ray transmission region 220 can be easily manufactured.

In this case, although the heat-resistant material of which the infrared ray transmission region 220 of the bowl 200 is made may be heat-resistant glass, tempered glass, crystal, or ceramic capable of transmitting infrared rays, the present embodiment is not limited thereto. The heat-resistant material may be replaced with one of various materials which are not excessively deformed by high-temperature infrared rays emitted by the infrared generator 400, which stably transmit infrared rays, and which does not cause a serious loss to infrared transmittance during the transmission of an infrared ray.

Meanwhile, the infrared ray transmission region 220 may be formed in a planar shape, and the area other than the infrared ray transmission region 220 may be formed in a concave arc shape.

In other words, the inner surface of the bowl 200 which temporarily accommodates excretions is formed in a concave arc shape. Accordingly, when infrared rays generated by the infrared generator are radiated into the bowl 200, infrared rays passing through the infrared ray transmission region 220 are diffused. The infrared ray transmission region 220 is formed in a planar shape in order to prevent infrared rays from being diffused and to allow infrared rays to be radiated onto the application region (the anus, the buttocks, etc.) of a user.

As another embodiment, the infrared ray transmission region 220 may be formed in a convex shape like a convex lens, and the area other than the infrared ray transmission region 220 may be formed in a concave arc shape. The reason for this is that infrared rays generated by the infrared generator 400 are concentrated and radiated onto the application region (the anus, the buttocks, etc.) of the user by forming the inner surface of the bowl 200, in which the infrared ray transmission region 220 is formed, in a convex shape like a convex lens.

Meanwhile, an opening 120 is formed through one side surface of the toilet body 100 corresponding to the infrared ray transmission region 220 of the bowl 200 in order to enable the infrared generator 400 to be inserted therethrough. Accordingly, the infrared generator 400 may be coupled into the toilet body 100 through the opening 120.

Figure 8:
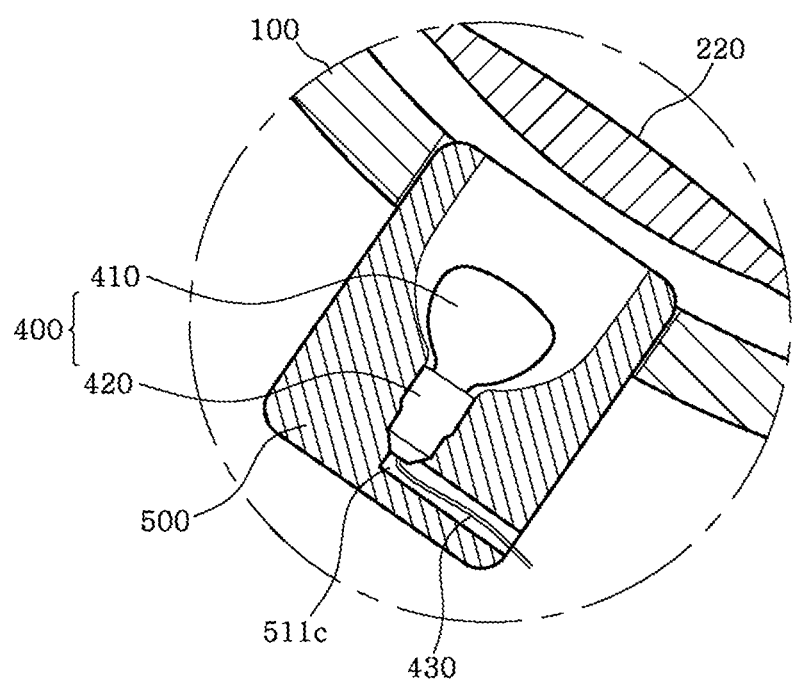
FIG. 8 is an enlarged view showing the coupled state of an outer cover according to the present invention.

As shown in FIG. 8, the infrared generator 400 or an outer cover 500 in which the infrared generator 400 is provided may be coupled into the opening 120.

The infrared generator 400 is provided in the outer cover 500, and the outer cover 500 in which the infrared generator 400 is provided is coupled into the opening 120. Accordingly, the infrared generator 400 is covered to be prevented from being exposed to the outside, and also the appearance of the toilet is made beautiful.

Although most of conventional toilets equipped with an infrared generator are configured to protect an infrared generator by using a bracket or case, they have a structure in which both the infrared generator and the bracket or case configured to protect the infrared generator are exposed to the outside of the toilet body. Accordingly, there is concern that unexpected external force is frequently applied to the exposed portion, so that there is high possibility that the infrared generator 400 is damaged and a problem, such as a failure attributable to the shutoff of power supply, may be caused, with the result that a problem arises in that the reliability of a product is deteriorated.

In order to overcome this problem, the present invention is configured such that the infrared generator 400 is accommodated in and protected by the outer cover 500 in order to prevent the infrared generator 400 from being exposed to the outside of the toilet body 100, so that the infrared generator 400 is prevented from being damaged due to an external factor and also a luxurious and beautiful appearance is provided.

Figure 9:
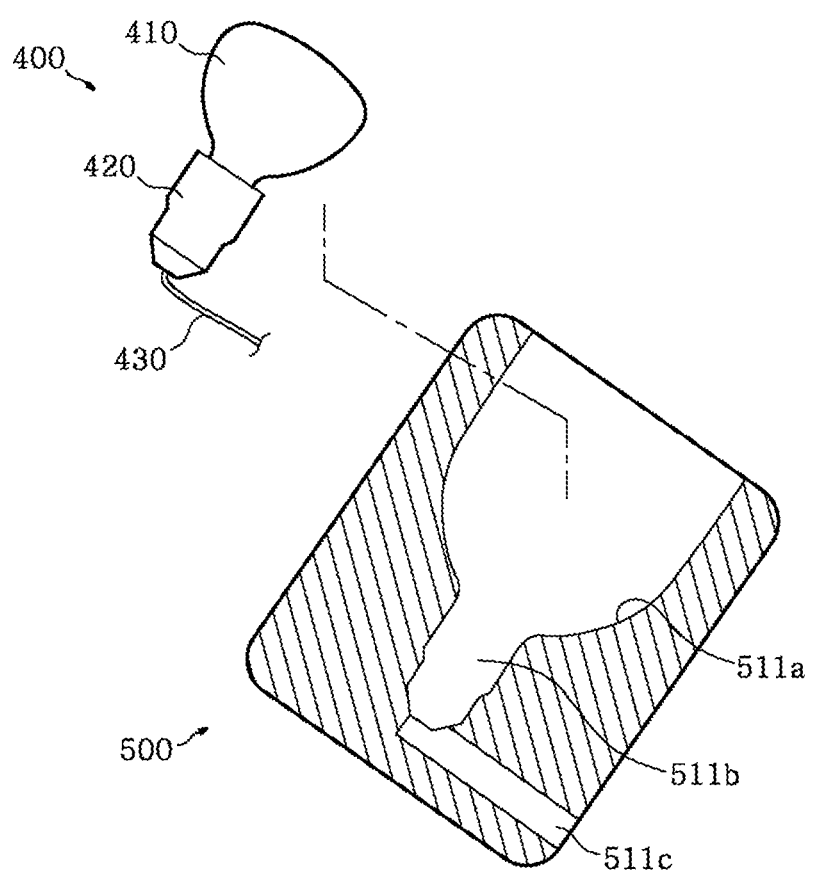
FIG. 9 is a sectional view showing the separated state of the outer cover and the infrared generator according to the present invention.

As shown in FIG. 9, the outer cover 500 includes: a hemispheric lamp seating cavity 511*a* in which the lamp 410 of the infrared generator 400 is seated; a socket coupling depression 511*b* which is formed to communicate with one side of the lamp seating cavity 511*a* and into which the socket 420 of the infrared generator 400 is coupled; and an electric wire exit hole 511*c* which is formed to communicate with one side of the socket coupling depression 511*b* and through which an electric wire 430 is led to the outside.

Conventionally, in order to install an infrared generator, a separate bracket, a separate heat-proof cap, a separate fastening rib, or the like is used and fastened using a bolt and a nut, so that an installation method is complicated and the bracket is exposed to the outside of a toilet after installation, thereby deteriorating the appearance of the toilet.

In order to overcome these problems, the present invention is provided with the infrared generator 400 inside the outer cover 500, and thus simplifies a coupling structure for the infrared generator provided in the toilet, so that advantages are provided in that the number of parts is reduced and maintenance and repair are facilitated.

Meanwhile, a coupling means may be provided on the outer circumferential surface of the outer cover 500 in order to be coupled and fastened into the opening 120.

Figure 10:
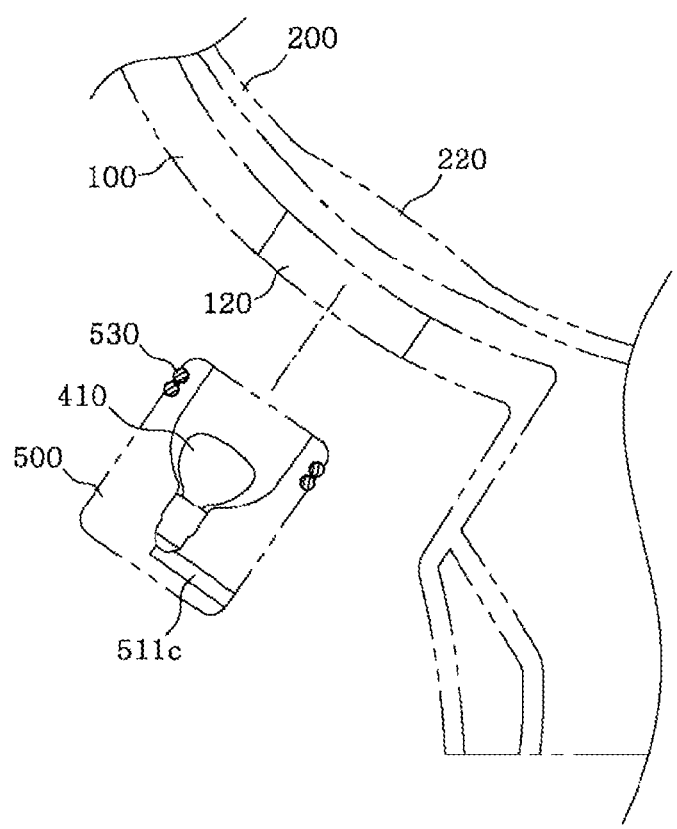
FIGS. 10 to 16 are exemplary views showing various embodiments of a coupling means and a fastening means according to the present invention.

FIG. 10 shows an embodiment of the coupling means. The coupling means is formed of a rubber packing 530 which is fitted over and coupled to the outer circumferential surface of the outer cover 500. This is intended to prevent the outer cover 500 from being removed to the outside by fastening the location of the outer cover 500 when the outer cover 500 is coupled into the opening 120.

Figure 11:
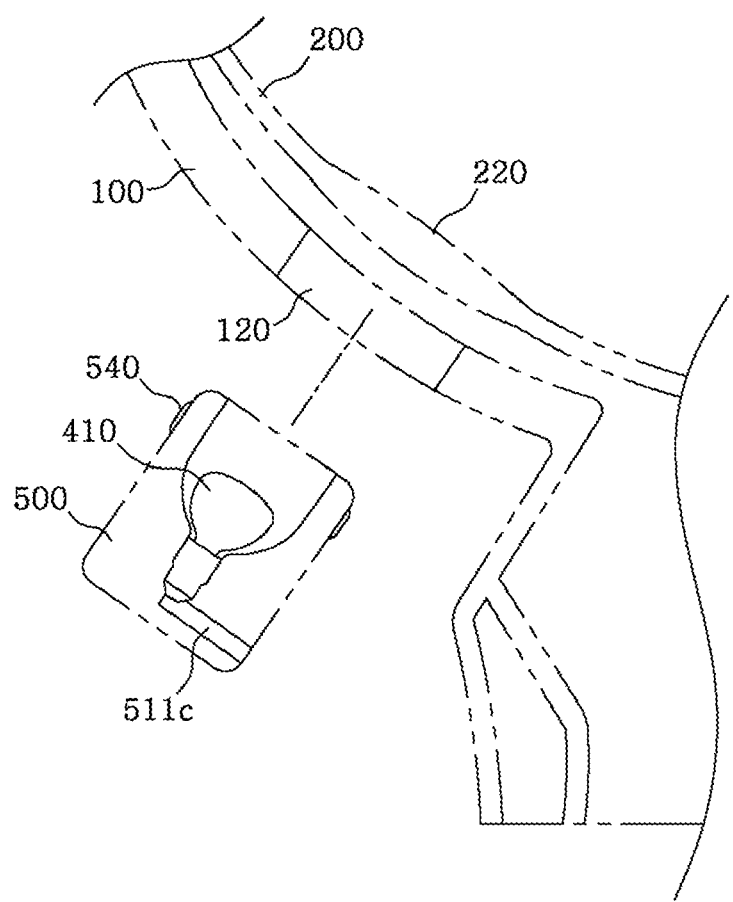

FIG. 11 shows another embodiment of a coupling means. The coupling means may be formed of a plurality of protrusions 540 which protrudes from the outer circumferential surface of the outer cover 500.

In other words, the plurality of protrusions 540 is formed on the outer circumferential surface of the outer cover 500, and can thus prevent the outer cover 500 from being removed from the opening 120 by securely fastening the outer cover 500 into the opening 120.

Meanwhile, a fastening means corresponding to the coupling means formed on the outer circumferential surface of the outer cover 500 may be provided on the inner surface of the opening 120. The coupling means and the fastening means may be formed in various structures.

Figure 12:
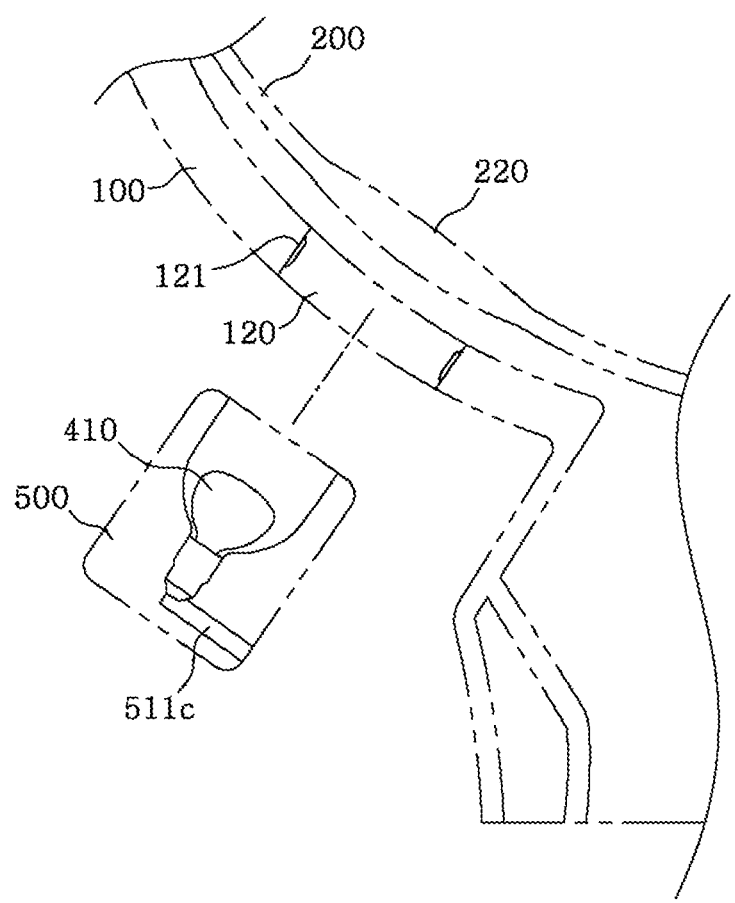

As shown in FIG. 12, the fastening means may be formed of a plurality of protrusions 121 which protrudes from the inner surface of the opening 120.

The protrusions 540 formed on the outer cover 500 may be omitted according to product design or manufacturing conditions. The protrusions 121 may be formed on the inner surface of the opening 120 in place of the omitted protrusions 540.

Figure 13A:
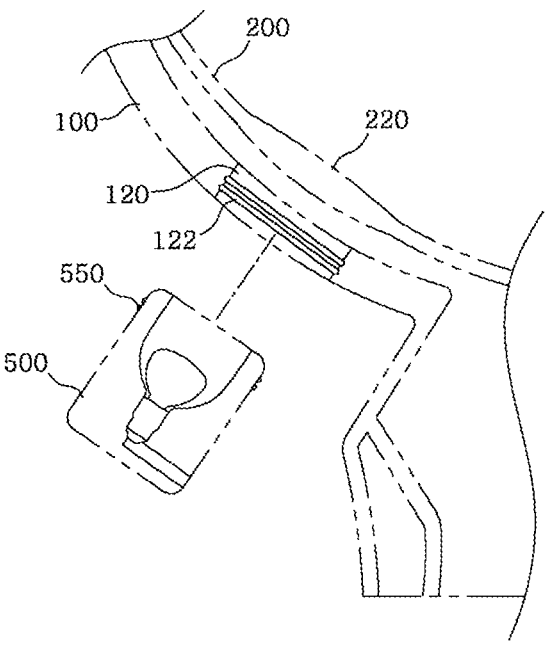

FIG. 13(a) shows still another embodiment of a coupling means and a fastening means. The coupling means may be formed of a fastening screw 550 formed on the outer circumferential surface of the outer cover 500, and the fastening means may be formed of a fastening screw 122 formed on the inner surface of the opening 120 to correspond to the fastening screw 550 of the coupling means.

Accordingly, the coupling and separation of the outer cover 500 is facilitated by tightening the fastening screw 550 formed on the outer circumferential surface of the outer cover 500 to the fastening screw 122 formed on the inner surface of the opening 120.

The fastening screw 122 formed on the opening 120 and the fastening screw 550 formed on the outer cover 500 may be formed interchangeably according to product design or manufacturing conditions.

Figure 13B:
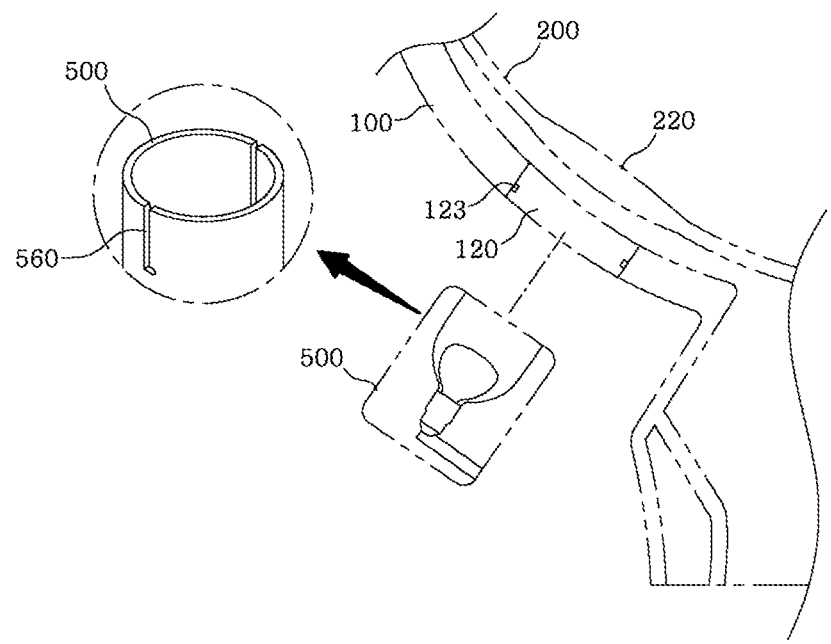

FIG. 13(b) shows still another embodiment of a coupling means and a fastening means. The coupling means may be formed of a plurality of fastening slits 560 formed in one end portion of the outer circumferential surface of the outer cover 500, and the fastening means may be formed of fastening protrusions 123 formed on the inner surface of the opening 120 to correspond to the fastening slit 560 of the coupling means.

Accordingly, the coupling and separation of the outer cover 500 is facilitated by fitting the fastening slits 560 formed in one end portion of the outer circumferential surface of the outer cover 500 into the plurality of fastening protrusions 123 formed on the inner surface of the opening 120.

The fastening protrusions 123 formed on the opening 120 and the fastening slits 560 formed in the outer cover 500 may be formed interchangeably according to product design or manufacturing conditions.

Figure 14:
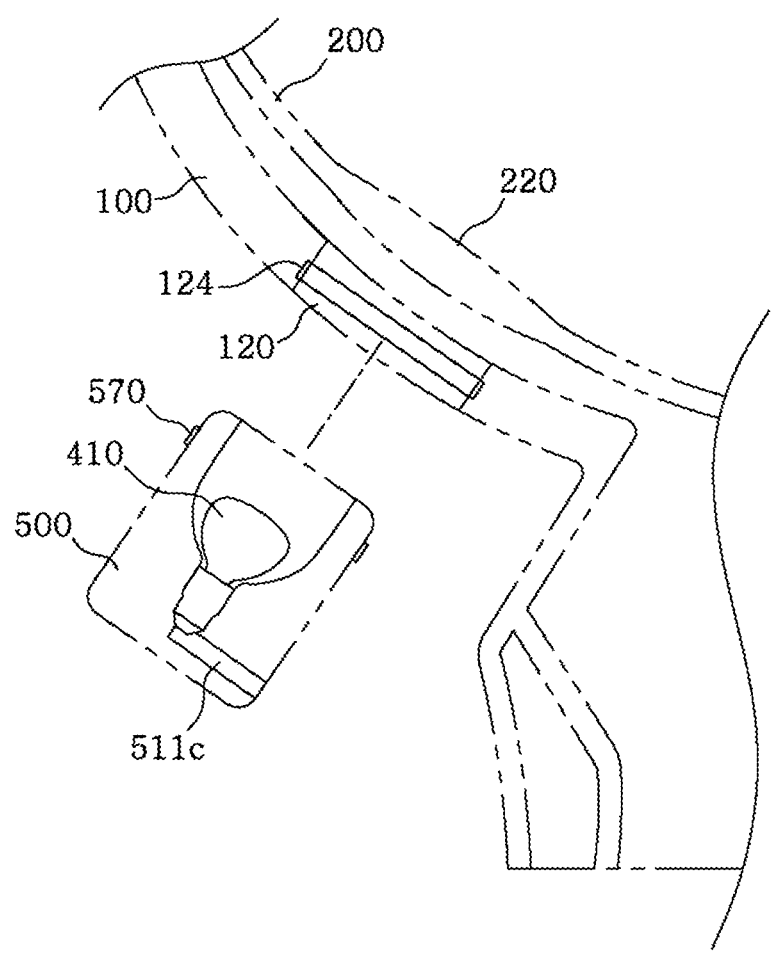

FIG. 14 shows still another embodiment of a coupling means and a fastening means. The coupling means may be formed of a magnet member 570 provided on the outer circumferential surface of the outer cover 500, and the fastening means may be formed of a metallic member 124 provided on the inner surface of the opening 120 to correspond to the magnet member 570 of the coupling means.

In other words, the metallic member 124 is provided on the inner surface of the opening 120, and the magnet member 570 is provided on the outer circumferential surface of the outer cover 500. Accordingly, when the outer cover 500 is coupled into the opening 120, the magnet member 570 is attached to the metallic member 124 by magnetic force, and thus securely fastens the outer cover 500, thereby preventing the outer cover 500 from being separated.

Figure 15:
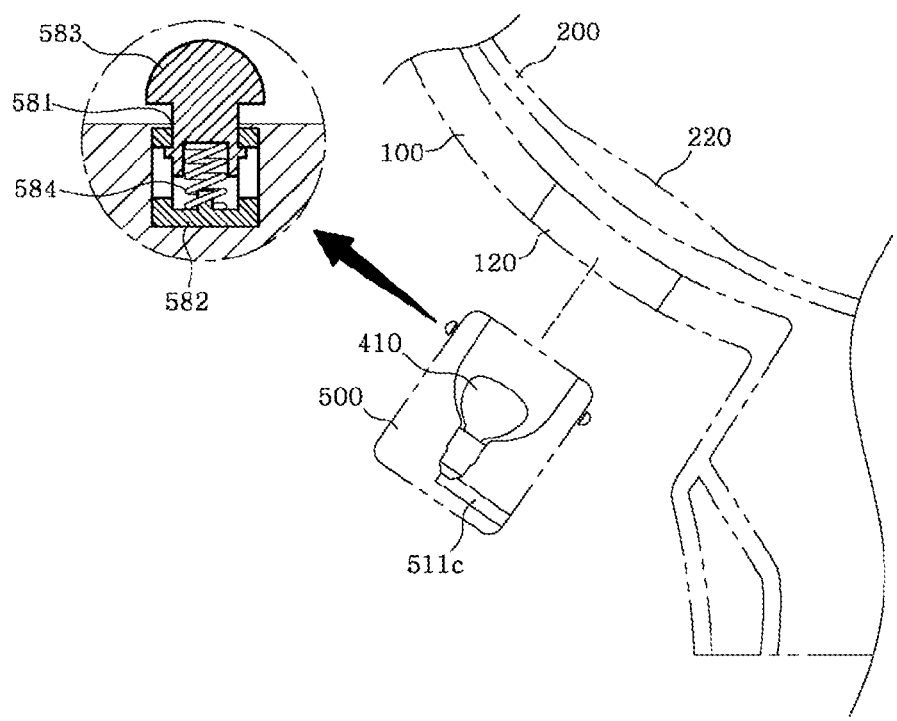

FIG. 15 shows still another embodiment of a coupling means and a fastening means. The coupling means may be formed of: a plurality of reception depressions 581 which is formed on the outer circumferential surface of the outer cover 500 to a predetermined depth; a cylindrical case 582 which is separably coupled into each of the reception depressions 581; a pressing protrusion 583 which is movably disposed inside the case 582; and a spring 584 which performs an elastic action in response to an impact applied to the pressing protrusion 583.

In other words, the outer cover 500 may be separably coupled to the inner surface of the opening 120 by an elastic coupling method. More specifically, the pressing protrusion 583 which is movably disposed inside the case 582 is elastically supported by the spring 584. When the outer cover 500 is coupled into the opening 120, the spring 584 continuously provides elastic force to the pressing protrusion 583, and thus securely fastens the outer cover 500, thereby preventing the outer cover 500 from being separated.

Figure 16:
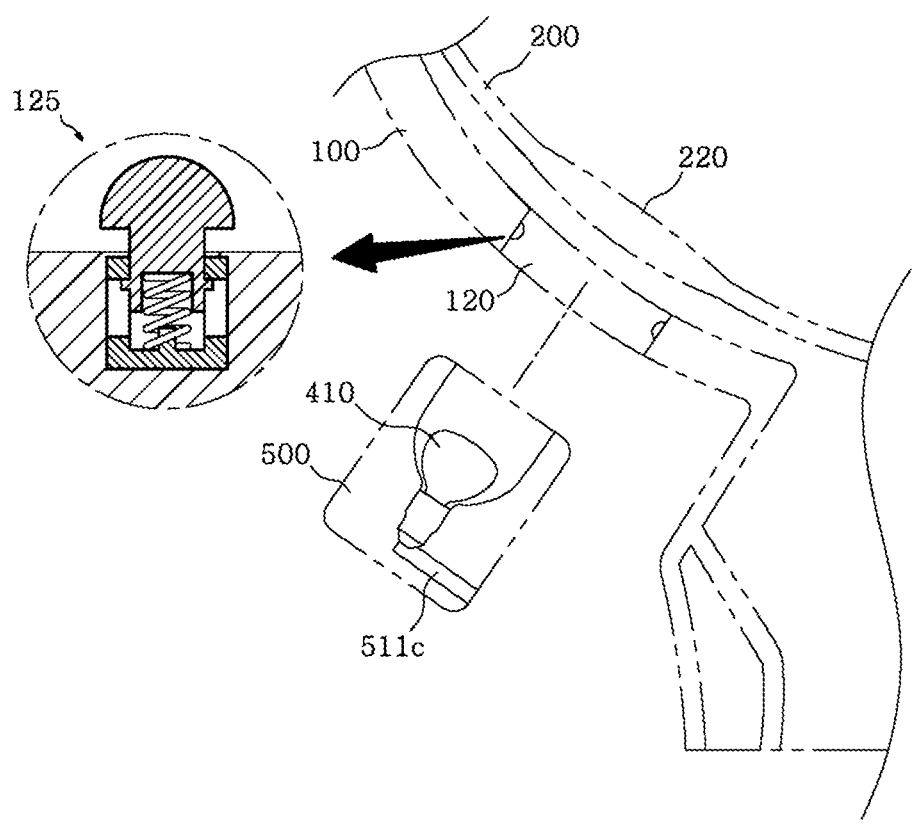

Meanwhile, as shown in FIG. 16, the coupling means (the reception depression, the case, the pressing protrusion, and the spring) provided on the outer circumferential surface of the outer cover 500 may be omitted according to product design or manufacturing conditions. An elastic support unit 125 including a reception depression, a case, a pressing protrusion, and a spring may be formed on the inner surface of the opening 120 in place of the omitted coupling means.

As described above, the time required to couple and separate the outer cover 500 can be reduced via the various coupling methods for the outer cover 500, a separate tool is not required to couple and separate the outer cover 500, and the outer cover 500 can be easily coupled and separated using a small amount of force.

As shown in FIGS. 17 to 20, a fastening element 600 into which an infrared generator 400 or an outer cover 500 in which the infrared generator 400 is provided is inserted and coupled may be provided in an opening 120.

The fastening element 600 is configured such that one side of the fastening element 600 is inserted into and stuck in the opening 120 of a toilet body 100 and the other side of the fastening element 600 supports a bowl 200 coupled inside the toilet body 100. Accordingly, the fastening element 600 can be coupled to the toilet body 100 without a separate fastening means, and the location of the fastening element 600 can be conveniently fastened.

Therefore, the fastening element 600 may be coupled to the toilet body 100 without a separate fastening means while stably supporting the bowl 200.

Although the fastening element 600 is formed in a cylindrical shape, it may be formed in any one of a circular shape, an elliptical shape, and a polygonal shape, but is not limited thereto. It may be formed in various shapes.

Since the infrared generator 400 is inserted and coupled into the fastening element 600, it is preferable that the fastening element 600 be disposed to be inclined downward toward the outside of the bowl 200 in order to facilitate the coupling and separation of the infrared generator 400.

Furthermore, the fastening element 600 is formed to be inclined downward so that infrared rays emitted by the infrared generator 400 are transmitted through the infrared ray transmission region 220 of the bowl 200 and radiated onto the application region (the anus, the buttocks, etc.) of a user sitting on the toilet. The fastening element 600 is formed in a shape corresponding to that of the infrared generator 400 or outer cover 500.

Figure 17:
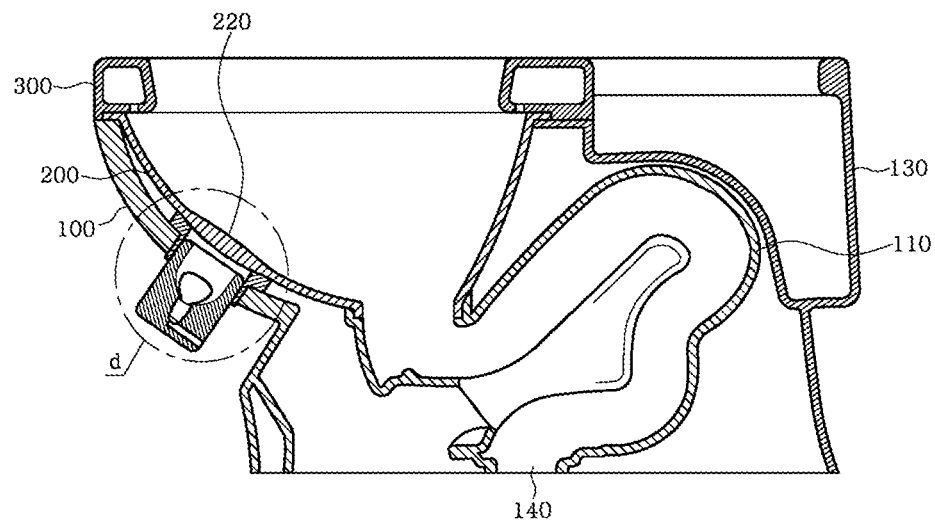
FIG. 17 is a sectional view showing a state in which a fastening element according to the present invention has been provided.
Figure 18:
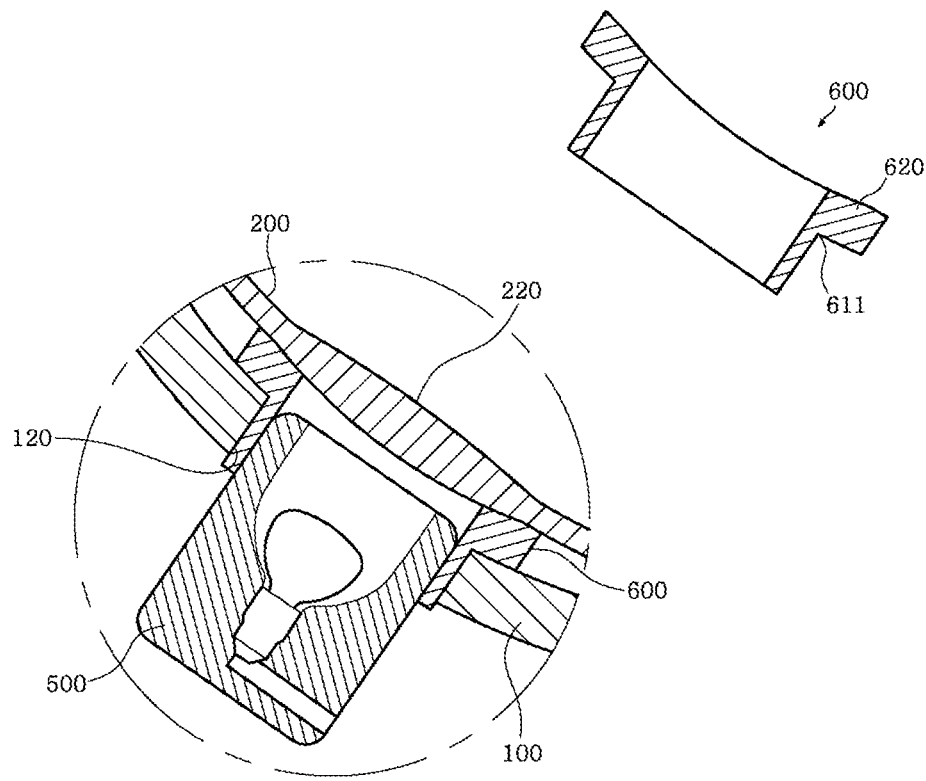
FIG. 18 is an enlarged view of portion 'd' of FIG. 17.

As shown in FIGS. 17 and 18, the fastening element 600 may include: a support portion 620 which is formed to support a portion around the infrared ray transmission region 220 of the bowl 200; and a stepped portion 611 which is formed in the outer side of the fastening element 600 to be coupled to a portion around the opening 120 of the toilet body 100.

In other words, the fastening element 600 supports the portion around the infrared ray transmission region 220 of the bowl 200 via the support portion 620 formed in the fastening element, and supports the bottom surface of the bowl 200 through surface contact. Furthermore, the fastening element 600 is stuck in and coupled to the circumference of the opening 120 of the toilet body 100 by the stepped portion 611 formed in the outer side of the fastening element 600.

Figure 19:
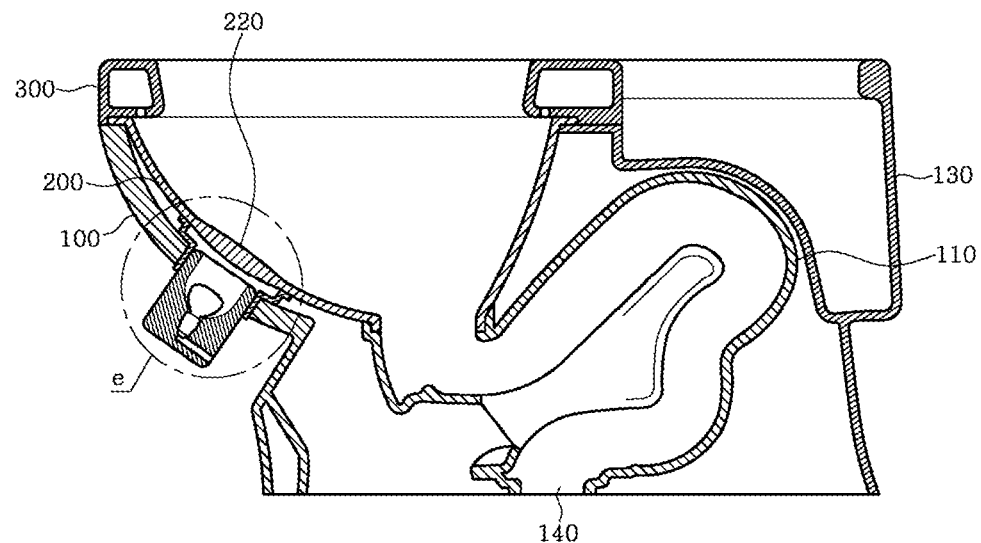
FIG. 19 is a sectional view showing another embodiment of a fastening element according to the present invention.
Figure 20:
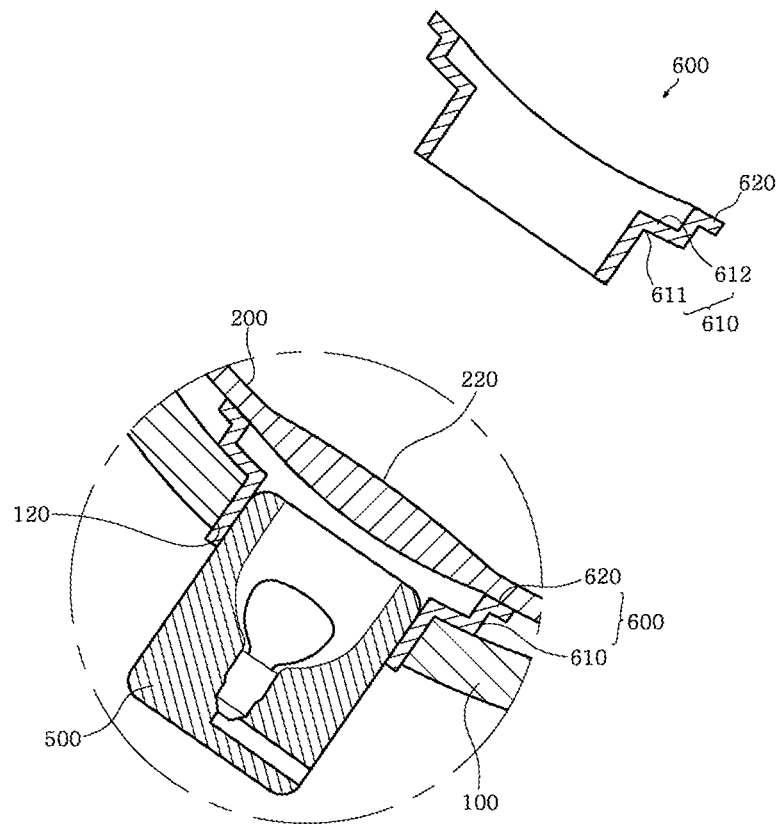
FIG. 20 is an enlarged view of portion 'e' of FIG. 19.

Furthermore, as shown in FIGS. 19 and 20, the fastening element 600 may be configured in a shape including: a body portion 610 in which a stop portion 612 having a stepped portion 611 to be coupled to the portion around the opening 120 of the toilet body 100 is formed; and a support portion 620 which protrudes and extends outward from an end of the body portion 610 and comes into surface contact with the bottom surface of the bowl 200.

Although this fastening element 600 has the advantage of being easily coupled into the opening 120 of the toilet body 100 due to the structure in which the stop portion 612 having the stepped portion 611 is formed, it may have insufficient coupling force. Accordingly, in the present invention, the other side of the fastening element 600 supports the portion around the infrared ray transmission region 220 of the bowl 200 through surface contact, and thus this support force allows both coupling force and coupling convenience with respect to the toilet body 100 to be fulfilled.

The support portion 620 is formed to have a larger diameter than the body portion 610. It is preferable that the support portion 620 be formed in a curved surface shape corresponding to the outer surface of the bowl 200.

Meanwhile, a fastening means which is the same as the fastening means having been provided in the opening 120 is provided in the fastening element 600, and a coupling means corresponding to the fastening means provided in the fastening element 600 may be provided in the outer cover 500 which is inserted and coupled into the fastening element 600. The coupling means is a coupling means which is the same as the coupling means having been provided in the outer cover 500 which is coupled to the opening 120.

Accordingly, the outer cover 500 may be separably coupled to the fastening element 600 by the coupling means provided in the outer cover 500 and the fastening means provided in the fastening element 600.

Figure 21:
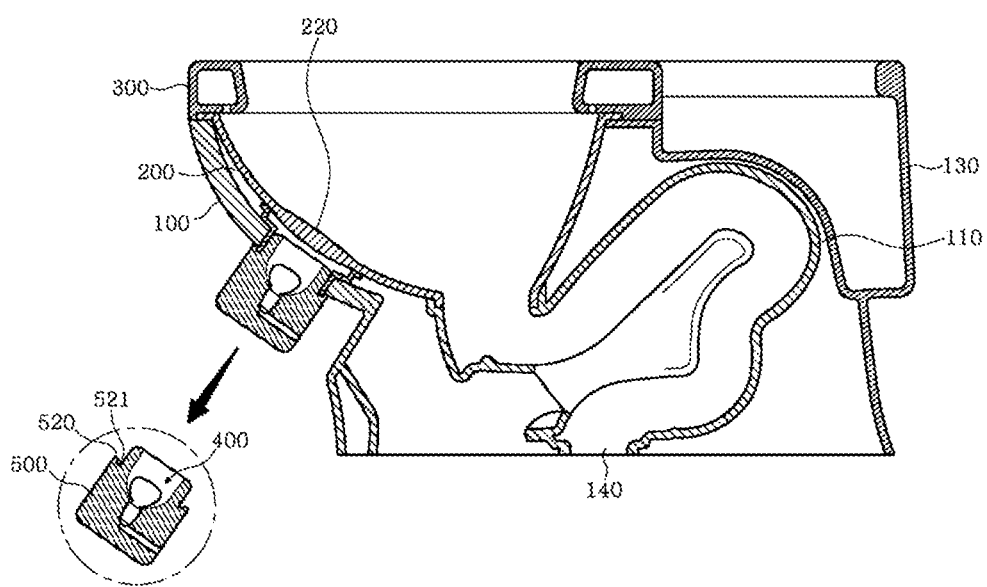
FIG. 21 is a sectional view showing another embodiment of an outer cover according to the present invention.

Meanwhile, as shown in FIG. 21, an outer circumferential portion 520 having a coupling groove 521 into the outer end of the fastening element 600 is inserted and coupled is formed on the outer surface of the outer cover 500.

Accordingly, the outer side of the fastening element 600 exposed to the outside is covered with the outer circumferential portion 520, thereby making the appearance of the toilet beautiful.

In this case, the fastening element 600 may be provided with a fastening means, and the outer circumferential portion 520 of the outer cover 500 may be provided with a coupling means. The outer end of the fastening element 600 is inserted and coupled into the coupling groove 521 of the outer cover 500 by the fastening means and the coupling means.

INDUSTRIAL APPLICABILITY

The toilet equipped with an infrared generator according to the present invention continuously emits infrared rays beneficial to the human body, thereby considerably contributing to the provision of disease treatment and prevention effects.

What is claimed is:

1. A toilet equipped with an infrared generator, the toilet comprising:
    a toilet body (100) a top of which is open, and in one side surface of which is formed an opening (120) configured to provide an infrared generator therein;
    a bowl (200) coupled inside the toilet body (100), the bowl having a first bent protrusion (201) formed at an upper end of the bowl, a second bent protrusion (202) formed at a lower end of the bowl, and an infrared ray transmission region (220) formed between the first and second bent protrusions without forming a hole,
    wherein an entire area of the infrared ray transmission region (220) is separated from the toilet body (100),
    wherein the infrared ray transmission region (220) of the bowl (200) is made of a material capable of transmitting infrared rays emitted by the infrared generator (400), wherein the infrared generator transmits the infrared rays at the infrared ray transmission region; and
    a rim conduit (300) which is coupled to the top of the toilet body (100) inside which the bowl (200) has been coupled,
    wherein the toilet body (100), the bowl (200), and the rim conduit (300) are integrated into a single body,
    wherein the infrared generator (400) is provided in the opening (120) of the toilet body.

2. The toilet of claim 1, wherein the first bent protrusion (201) is configured to be coupled to a top surface of the toilet body (100) which is formed along a circumference of the upper end of the bowl (200), and the second bent protrusion (202) is configured to be coupled to a stepped portion (111) formed on an inner surface of an upper end of a trap (110) which is formed along a circumference of the lower end of the bowl (200).

3. The toilet of claim 1, wherein:
    a stepped part protruding downward is formed on an outer side of a bottom of the rim conduit (300) which is coupled to tops of the toilet body (100) and the bowl (200);

a first seating protrusion (301) protrudes downward from the outer side of the bottom of the rim conduit (300) forming the stepped part; and an outer surface of the first seating protrusion (301) forms a same outer surface as an outer surface of the toilet body (100).

4. The toilet of claim 1, wherein:

a second seating protrusion (330) protruding downward is formed on an inner side of a bottom of the rim conduit (300) which is coupled to tops of the toilet body (100) and the bowl (200);

an outer surface of the second seating protrusion (330) is attached to an inner surface of the top of the bowl (200); and the rim conduit (300) is coupled to the toilet body (100) and the bowl (200) in a state of surrounding the toilet body (100) and the bowl (200) by the second seating protrusion (330).

5. The toilet of claim 4, wherein:

a support (150) configured to support the bowl (200) is provided on a bottom of an inside of the toilet body (100); and a connection element (160) configured to connect the bowl (200) and a trap (110) is provided on a top of the support (150).

6. The toilet of claim 1, wherein a finishing member (700) is attached to a circumference of adhered surfaces of the toilet body (100) and the rim conduit (300).

7. The toilet of claim 1, wherein the bowl (200) is formed in any one of transparent, translucent, and opaque colors through which infrared rays emitted by the infrared generator (400) are transmitted.

8. The toilet of claim 7, wherein the translucent or opaque color in which the bowl (200) is formed is formed by coating an inner or outer surface of the bowl (200) with an infrared generation material.

9. The toilet of claim 7, wherein the translucent or opaque color in which the bowl (200) is formed is formed by an infrared generation material added during injection molding of the bowl (200).

10. The toilet of claim 1, wherein the bowl (200) is made of any one of glass, plastic, and ceramic.

11. The toilet of claim 1, wherein the infrared ray transmission region (220) and an area of the bowl (200) other than the infrared ray transmission region (220) are formed in an integrated manner, the infrared ray transmission region (220) is made of a heat-resistant material capable of withstanding high-temperature infrared rays emitted by the infrared generator (400), and the area other than the infrared ray transmission region (220) is made of a plastic or ceramic material.

12. The toilet of claim 1, wherein a part of an inner surface of the bowl (200) where the infrared ray transmission region (220) is formed is formed in a planar shape, and an area other than the infrared ray transmission region (220) is formed in a concave arc shape.

13. The toilet of claim 1, wherein a part of an inner surface of the bowl (200) where the infrared ray transmission region (220) is formed is formed in a convex shape, and an area other than the infrared ray transmission region (220) is formed in a concave arc shape.

14. The toilet of claim 1, wherein: the infrared generator (400) is provided inside an outer cover (500); and the outer cover (500) inside which the infrared generator (400) has been provided is provided in the opening (120).

15. The toilet of claim 1, wherein:

the opening (120) is further provided with a fastening element (600); and the infrared generator (400) or an outer cover (500) inside which the infrared generator (400) has been provided is inserted and fastened into the fastening element (600).

* * * * *